United States Patent
Stenzler et al.

(10) Patent No.: US 10,500,358 B2
(45) Date of Patent: Dec. 10, 2019

(54) GAS REGULATOR WITH INTEGRATED SENSORS

(71) Applicant: 12th Man Technologies, Inc., Garden Grove, CA (US)

(72) Inventors: Alex Stenzler, Long Beach, CA (US); Steve Han, Huntington Beach, CA (US)

(73) Assignee: 12th Man Technologies, Inc., Garden Grove, CA (US)

( * ) Notice: Subject to any disclaimer, the term of this patent is extended or adjusted under 35 U.S.C. 154(b) by 276 days.

(21) Appl. No.: 14/075,402

(22) Filed: Nov. 8, 2013

(65) Prior Publication Data

US 2014/0130799 A1    May 15, 2014

Related U.S. Application Data

(60) Provisional application No. 61/724,433, filed on Nov. 9, 2012.

(51) Int. Cl.
*F17C 13/04*    (2006.01)
*A61M 16/20*    (2006.01)
*A61M 16/00*    (2006.01)
*A61M 16/12*    (2006.01)

(52) U.S. Cl.
CPC ......... *A61M 16/0051* (2013.01); *F17C 13/04* (2013.01); *A61M 16/12* (2013.01);
(Continued)

(58) Field of Classification Search
CPC ...... A61M 15/00; A61M 16/00; A61M 16/01; A61M 16/16; A61M 16/18; A61M 16/22;
H04Q 5/22; F17C 13/003; F17C 13/04; F17C 2270/025; F17C 7/00; F16K 1/304; F16K 1/32; G05D 7/00
See application file for complete search history.

(56) References Cited

U.S. PATENT DOCUMENTS

| | | | |
|---|---|---|---|
| 8,573,210 B2 | 11/2013 | Bathe et al. | |
| 2005/0247371 A1* | 11/2005 | Chadbourne | B67D 1/0835 141/351 |

(Continued)

OTHER PUBLICATIONS

Nikitin, P. et al, "Performance Limitations of Passive UHF RFID Systems." (2006)http://www.ee.washington.edu/faculty/nikitin_pavel/papers/APS_2006.pdf.*

*Primary Examiner* — Peter S Vasat
(74) *Attorney, Agent, or Firm* — Riverside Law LLP

(57) ABSTRACT

A gas regulator is described. The gas regulator includes a gas inlet having an attachment mechanism for attaching to a gas container, a gas outlet in fluid communication with the gas inlet and further in fluid communication with a gas delivery system, a pressure regulator, a pressure sensor and a NFC sensor. A method of entering at least one information item relating to a gas source to a gas delivery system control unit. The method includes the steps of providing a gas source having a NFC tag that includes at least one information item stored in a memory of the NFC tag, attaching a regulator that includes a NFC sensor, wherein the NFC sensor is positioned to read the NFC tag when attached to the gas source, reading the at least one information item via the NFC sensor, and transmitting the at least one information item read by the NFC sensor to a gas delivery system control unit.

18 Claims, 4 Drawing Sheets

(52) U.S. Cl.
CPC ..... *A61M 16/20* (2013.01); *A61M 2016/0027* (2013.01); *A61M 2205/3561* (2013.01); *A61M 2205/3584* (2013.01); *A61M 2205/3592* (2013.01); *A61M 2205/50* (2013.01); *A61M 2205/6018* (2013.01); *A61M 2205/6054* (2013.01); *A61M 2205/8206* (2013.01); *F17C 2201/0109* (2013.01); *F17C 2201/032* (2013.01); *F17C 2201/056* (2013.01); *F17C 2201/058* (2013.01); *F17C 2205/0329* (2013.01); *F17C 2205/0338* (2013.01); *F17C 2205/0382* (2013.01); *F17C 2205/0394* (2013.01); *F17C 2205/058* (2013.01); *F17C 2221/011* (2013.01); *F17C 2221/03* (2013.01); *F17C 2250/034* (2013.01); *F17C 2270/025* (2013.01)

(56) References Cited

U.S. PATENT DOCUMENTS

| | | | |
|---|---|---|---|
| 2008/0011785 A1* | 1/2008 | Braun | B67D 7/0294 222/400.7 |
| 2008/0250564 A1* | 10/2008 | Stryker | A61G 7/001 5/615 |
| 2009/0050218 A1* | 2/2009 | Burgess | F17C 13/06 137/557 |
| 2009/0266358 A1* | 10/2009 | Sacristan Rock | A61M 16/104 128/203.26 |
| 2013/0000643 A1* | 1/2013 | Bathe | A61M 16/20 128/204.22 |

\* cited by examiner

GAS REGULATOR WITH INTEGRATED SENSORS

CROSS-REFERENCE TO RELATED APPLICATION

The present application claims priority under 35 U.S.C. 119(e) to U.S. Provisional Patent Application No. 61/724,433, filed Nov. 9, 2012, which is herein incorporated by reference in its entirety.

BACKGROUND OF THE INVENTION

Gases that are used for therapeutic purposes are typically provided in containers, such as cylinders, that are required to have specific threads on their valves to help identify different types of gases and to prevent a mix up of such gases during treatment. However, there are often times the availability of different concentrations of therapeutic gases that come in the same type of cylinder and with the same type of valve, which can ultimately cause confusion as to how much gas is being delivered during treatment. Additionally, the United States Food and Drug Administration may allow up to a 10 percent variation in gas concentration in the cylinder from the nominal concentration on the cylinder label. It is therefore important for healthcare providers or others using therapeutic gas delivery equipment to know what the starting concentration of each cylinder is, particularly when mixing gases to titrate a precise dose. Further, knowing the actual concentration being drawn from the gas cylinder can improve the accuracy of the dose delivered to a patient.

Gas cylinders are typically stored in outside storage facilities or in less than optimally clean rooms. The cylinders are therefore frequently exposed to dust and dirt and external labels, especially those that must be read by optical scanning methods (e.g., bar codes, etc.), may be obscured and ultimately miscommunicated to the controller or operator.

Further, many gas delivery systems require that more than one cylinder be available for the patient so that there is no interruption of gas delivery. Typically, only one cylinder has its valve open to deliver gas, while a backup cylinder is next to the device with its valve closed. When broad range or optical sensors are used to identify cylinders in use, the system may not be able to determine the actual information about the gas cylinder supplying gas unless it is known whether the valve is open, and therefore providing gas to the system.

Thus, there is a continuing need in the art for a gas delivery regulator that can collect information about the gas from the cylinder or container holding the gas. The present invention addresses this unmet need in the art.

SUMMARY OF THE INVENTION

The present invention relates to a gas regulator with a Near Field Communication (NFC) sensor. In one embodiment, the gas regulator of the present invention may also comprise a gas inlet having an attachment mechanism for attaching to a valve assembly of a gas container, a gas outlet in fluid communication with the gas inlet and further in fluid communication with a gas delivery system, and a pressure regulator. In one embodiment, the gas regulator may further comprise a pressure sensor.

The NFC sensor of the present invention can be positioned within close proximity to a NFC tag positioned on the gas container when the regulator is attached to the gas container. In one embodiment, the NFC sensor may comprise a NFC reader. In one embodiment, the gas regulator can be communicatively connected to a gas delivery system control unit. In one embodiment, the gas regulator of the present invention transmits data read from the NFC tag to the gas delivery system control unit. In one embodiment, the data read from the NFC tag can be selected from the group consisting of gas type, gas concentration, gas volume, gas expiration date, gas container owner, gas container size, and gas tank inspection dates. In one embodiment, a signal indicative of sensed pressure by the pressure sensor can be transmitted to the gas delivery control unit. In one embodiment, the pressure regulator can be controlled by the control unit.

The present invention also relates to a method of entering at least one information item relating to a gas source to a gas delivery system control unit, comprising the steps of: providing a gas source having a NFC tag that includes at least one information item stored in a memory of the NFC tag; attaching a regulator that includes a NFC sensor, wherein the NFC sensor is positioned to read the NFC tag when attached to the gas source; reading the at least one information item via the NFC sensor; and transmitting the at least one information item read by the NFC sensor to a gas delivery system control unit.

The present invention also relates to a method of controlling flow of a therapeutic gas to a gas delivery system, comprising the steps of: providing a gas source having a NFC tag that includes at least one information item stored in a memory of the NFC tag; attaching a regulator that includes a NFC sensor, wherein the regulator includes a gas inlet and outlet and is in fluid communication with a gas delivery system, and wherein the NFC sensor is positioned to read the NFC tag when attached to the gas source; reading the at least one information item via the NFC sensor; transmitting the at least one information item read by the NFC sensor to a gas delivery system control unit; and controlling the flow of gas based on the transmitted at least one information item.

In one embodiment of the methods of the present invention, the information item can be selected from the group consisting of gas type, gas concentration, gas volume, gas expiration date, gas container owner, gas container size, and gas tank inspection dates. In another embodiment, the methods of the present invention can further comprise sensing the pressure of gas from the gas source via a pressure sensor positioned in the regulator, and transmitting a signal indicative of the sensed pressure to the gas delivery system control unit.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A is a perspective view of a gas regulator, while FIG. 1B illustrates the internal components of the gas regulator of FIG. 1A.

FIGS. 3A and 3B, is an illustration of a control unit for delivery of a gas to a patient, according to an aspect of the present invention.

DETAILED DESCRIPTION

Figure 1A:
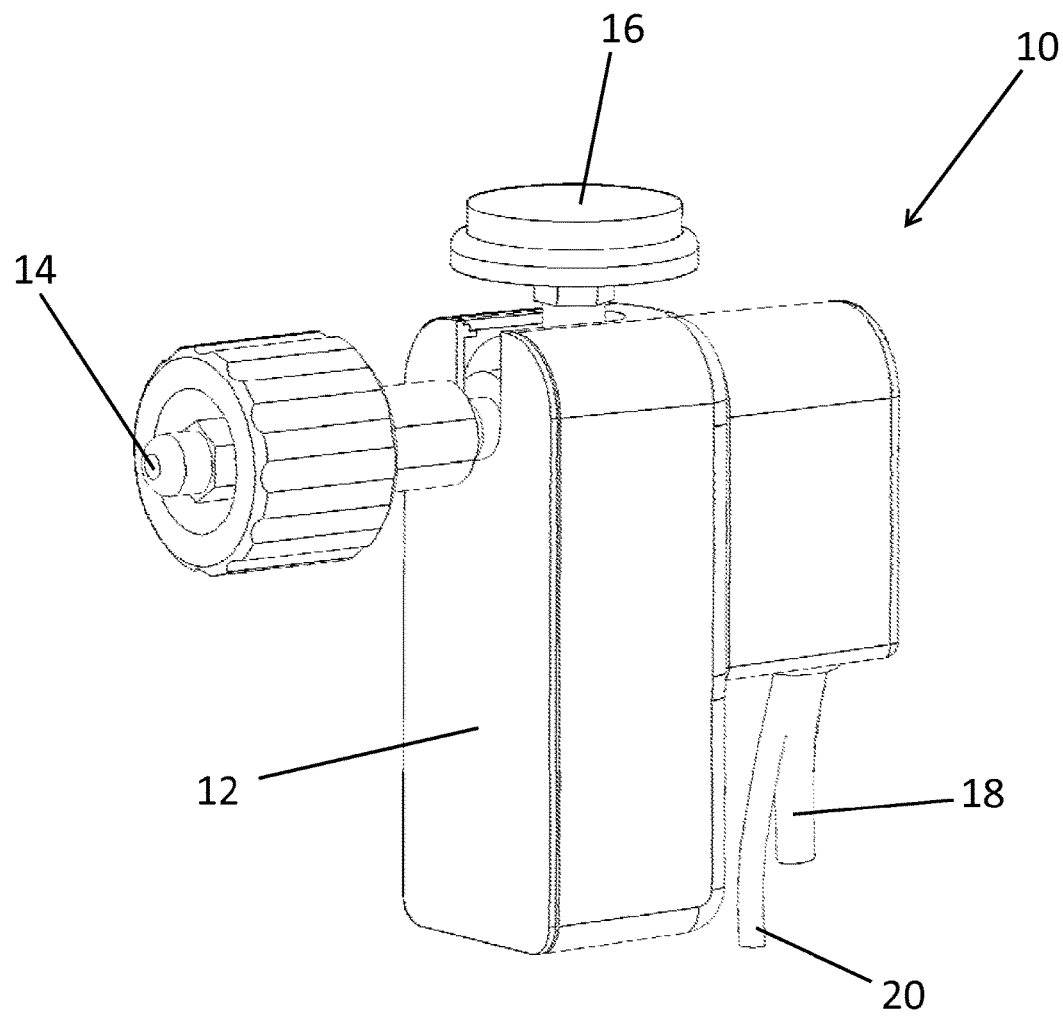
FIGS. 1A and 1B, is a schematic diagram of an exemplary gas regulator, according to an aspect of the present invention.

It is to be understood that the figures and descriptions of the present invention have been simplified to illustrate elements that are relevant for a clear understanding of the present invention, while eliminating, for the purpose of clarity, many other elements found in gas regulators and gas delivery systems. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods, materials and components similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

The terms "gas container," "gas cylinder," "tank," "gas source," and the like can be used interchangeably herein, and refer to any type of vessel suitable for storing and/or delivering gases.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

The present invention relates to a gas regulator with a Near Field Communication (NFC) sensor that can read data indicative of information relating to the contents of a gas cylinder, such as the type of gas, its concentration, its expiration date, its volume, the tank owner, tank testing or inspection dates, tank size, or other relevant information about the gas cylinder, from an NFC passive tag or label positioned on or in close proximity to the gas cylinder to which the information applies. In certain embodiments, the gas regulator also includes a pressure sensor for sensing gas pressure from the cylinder to which it is attached, to identify whether the cylinder valve is open, if the cylinder is nearing empty or empty, or possibly if the cylinder is compromised in such a way that pressure is affected. The regulator may be attached directly to the valve of the cylinder, such that the NFC sensor is within close proximity to the cylinder NFC passive tag and reading only the information of the cylinder it is attached to.

Figure 1B:
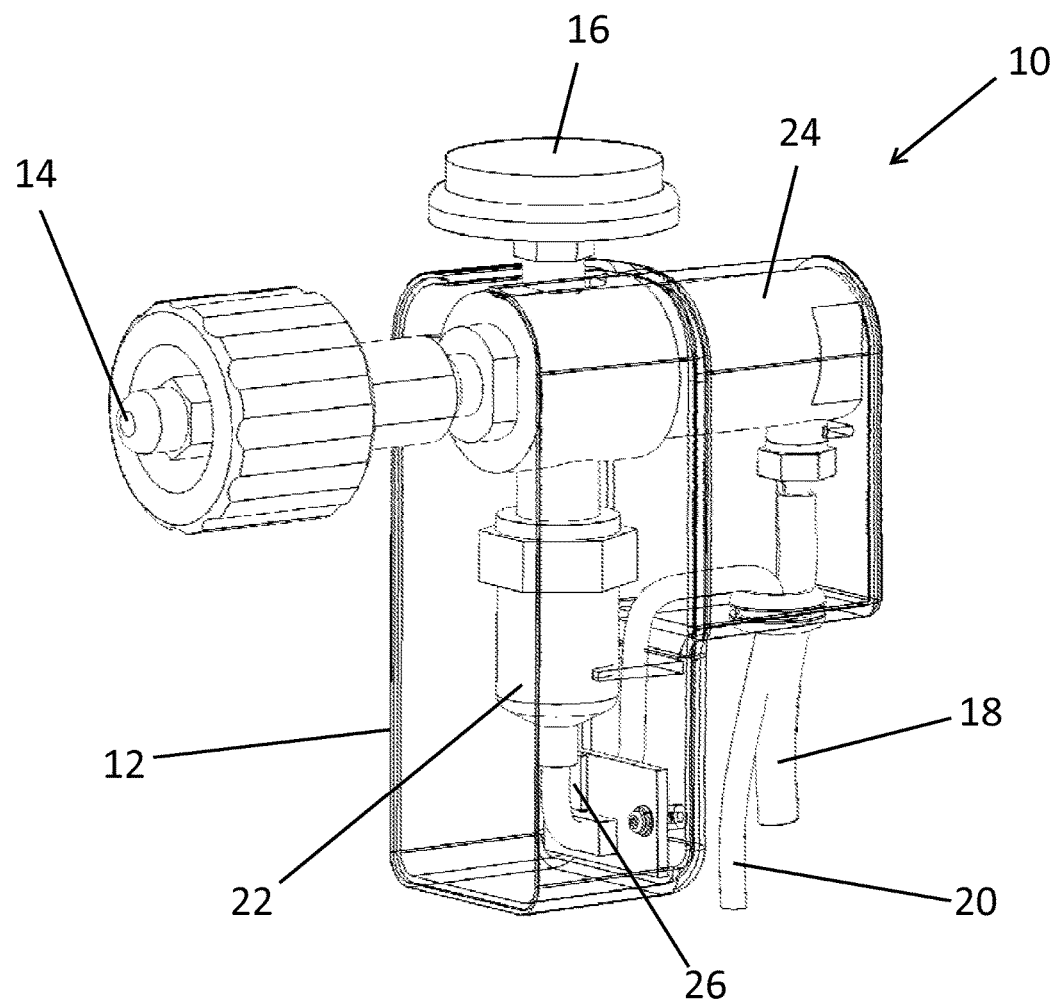

For example, as shown in FIGS. 1A and 1B, regulator 10 generally includes a housing 12, a gas cylinder inlet and connector 14, a pressure gauge 16, a gas outlet 18 and signal outlet 20. Signal outlet 20 may also be used to connect with and power any electrical component of regulator 10, or each such electrical component may utilize a power line running alongside but separately from signal outlet 20 to a power source outside of regulator 10. Inside housing 12 also resides a pressure sensor 22, a pressure regulator 24 and a near field communications (NFC) sensor 26. In alternative embodiments, regulator 10 may further include a power source, at least one microprocessor, additional signal transceiver(s) and at least one memory, and having resident therein any sort of system software or protocol executable by regulator 10. In other words, regulator 10 may be constructed so as to independently function as its own wired or wireless communication device capable of receiving and transmitting data to other computing or communications device.

Figure 2:
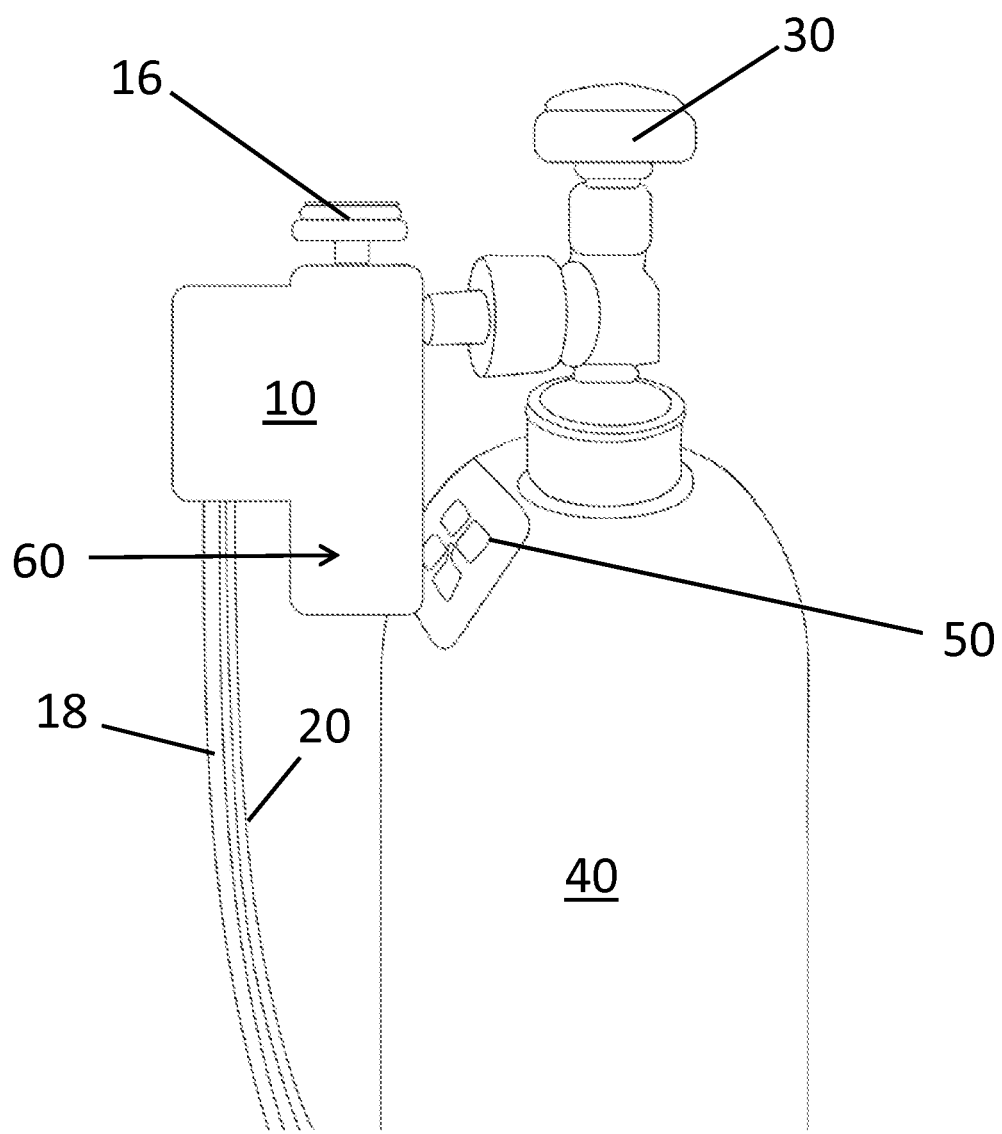
FIG. 2 is a schematic diagram of an exemplary gas regulator attached to a gas cylinder, according to an aspect of the present invention.
Figure 3:
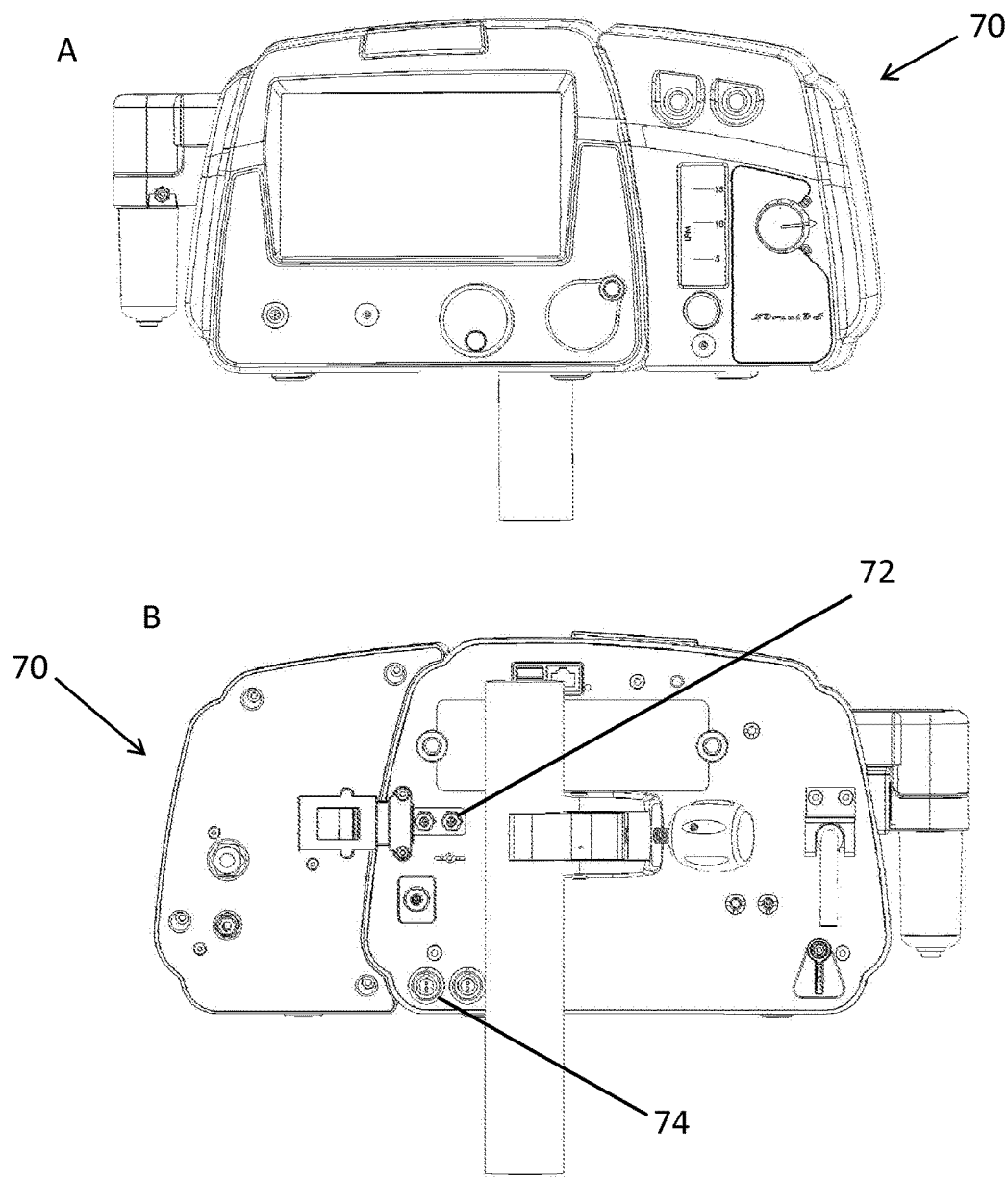
FIG. 3, comprising

As contemplated herein, regulator 10 may attach to a gas source (such as via a valve) and create a path for gas flow from cylinder connector 14 and ultimately exiting via gas outlet 20 to a gas delivery system control unit such as is shown in FIG. 3 or other device. Cylinder connector 14 may be a standard screw thread connection and sealing mechanism to a gas cylinder valve assembly, such as valve assembly 30 of FIG. 2, or any other connection mechanism suitable for connecting to a gas source, such as a pin index mechanism, as would be understood by those skilled in the art.

Regulator 10 can include along the gas flow path any component suitable for measuring, sensing, or sampling any parameter of the gas traveling therethrough. For example, the gas flow path may include a Bourdon tube or diaphragm pressure gauge 16 for mechanically measuring and allowing a user to visually identify on the gauge the pressure of gas flow traveling therethrough. Pressure gauge 16 may be any type of gauge for measuring absolute or differential pressures as would be understood by those skilled in the art, such as a Wika® pressure gauge.

Regulator 10 may also include pressure sensor 22, which may be an electrical transducer for converting sensed pressure to an electrical signal deliverable to a control unit. Pressure sensor 22 may be any sort of inductive, resistive, or capacitive sensor as would be understood by those skilled in the art, such as an Elotek® 09-4019 pressure transducer. Output signals from pressure sensor 22 may exit regulator 10 via signal outlet 20 to a control unit or other computing device.

Regulator 10 may further include pressure regulator 24 for increasing or reducing pressure of the system, and ultimately assisting in the control of gas flow through regulator 10. Pressure regulator 24 may be communicatively connected to and receive signals from a control unit via signal outlet 20, or from pressure sensor 22 (directly or indirectly) to open and shut the valve components integrated within it. Pressure regulator 24 may include additional pressure sensors, or any other standard component of a pressure regulator as would be understood by those skilled in the art. By non-limiting example, pressure regulator may be a Premier Industries 50-11502 regulator.

Regulator 10 also includes NFC sensor 26 for reading and transmitting data received from another NFC enabled device or tag that is associated with the gas cylinder to which regulator 10 is attached. As contemplated herein, the integrated NFC technology provides regulator 10 with a contactless short-range communications system based on radio-frequency identification (REID) standards, using magnetic field induction to enable communication between regulator 10 and another NFC enabled electronic device or passive tag. Examples of NEC tags include, but are not limited to: a Sony® FeliCa® RC-S801, RC-S802 or RC-S926 dynamic tag, or a SMARTRAC BULLSEYE, CIRCUS, or MINI-TRACK tag. Examples of NFC sensors or readers include, but are not limited to: ON TRACK INNOVATIONS (OTI) SCI readers or Sony® NFC readers. By utilizing a NFC based communication system, information can be transmitted wirelessly and without the need for a line of site, such as in other optical communication systems.

While the present invention is not restricted from using optical communication systems, NEC technology is preferred, because the system is not interrupted by dirty or obscured gas cylinder labels, and further necessitates that the gas cylinder NFC tag is in close proximity to the regulator to prevent the regulator from collecting data from the wrong tag (such as a tag for a cylinder nearby but not currently in use). In one exemplary embodiment, the integrated NFC system may operate at 13.56 MHz and with an effective range of about 10 cm. In alternative embodiments, other suitable versions of NFC may have different operating frequencies, effective ranges, etc., as would be understood by those skilled in the art. While the communication sensor component of regulator 10 is generally described and depicted as a NFC sensor, it should be appreciated that any wireless communications system, for example any other form of radio technology or radio-frequency identification (RFID), can be used to read or otherwise transmit data from the gas source (cylinder) and the regulator or system control unit via regulator 10.

Referring again to FIG. 1B, NFC sensor 26 may include a NFC transceiver or "reader," which is communicatively coupled to a control unit such as illustrated in FIG. 3, the control unit including a NEC controller or processor, integrated circuit (IC) and a first memory coupled with the NFC controller and capable of storing a NEC protocol and/or set of NEC based applications. Alternatively, sensor 26 may include a NFC controller or processor, IC, NFC tag, and memory and resident applications, instead of or in addition to such components being located in the control unit.

While regulator 10 is not limited to any particular size and shape, regulator 10 is preferably proportioned to promote easy attachment to the gas outlet of a gas cylinder or valve assembly and at the same time have NFC sensor 26 within a suitable range to read a NFC tag or label associated with the attached gas cylinder. For example, as shown in FIG. 2, regulator 10 is attached to the gas outlet of a valve assembly 30, which is itself attached to a gas source, such as gas cylinder 40. With regulator 10 effectively attached to gas cylinder 40 via valve assembly 30 for the delivery of gas to a gas delivery system and control unit, such as the control unit of FIGS. 3A and 3B, the NFC sensor being positioned in region 60 of regulator 10 is capable of recognizing and reading NFC tag 50 positioned on gas cylinder 40. As contemplated herein, NFC tag 50 may be programmed and/or applied to the cylinder by any person or entity prior to attachment to regulator 10, such as by the gas manufacturer, distributor, delivery system operator or any other suitable source. The information may be entered into the memory of NFC tag 50 by standard means, and may include information such as, but not limited to, the type of gas, its concentration, its expiration date, the tank owner, tank testing or inspection dates, or other relevant information about the gas cylinder. NFC tag 50 may be fixedly attached and secured to a surface of gas cylinder 40, or it may be adjustably secured to gas cylinder 40, such as attachment via a cord or tying means. It should be appreciated that NFC tag 50 may be attached and positioned at any location of gas cylinder 40, provided that such attachment and positioning is in proximity of region 60 of regulator 10 suitable for reading by the NFC reader component of regulator 10.

As contemplated herein, the present invention may be used with any gas delivery system as would be understood by those skilled in the art, particularly therapeutic gas delivery systems for delivering therapeutic dosages of gases such as nitric oxide, oxygen and anesthetics, for example, and especially for gas blending systems that require accurate and real-time measurement of the different gas concentrations and pressures being fed into the delivery system. For example, as shown in FIG. 3, the regulator of the present invention may feed a control unit 70, such as an INOvent® Nitric Oxide Delivery System for managing the delivery of the therapeutic gas to a patient. FIG. 3A is a front view of a control unit 70 operator interface, including a visual display, means for entering patient or system data, and all standard components necessary for operating the control unit as would be understood by those skilled in the art. FIG. 3B illustrates the back view of control unit 70, having one or more gas inlets 72 fed from and in fluid communication with the regulator of the present invention, and one or more electronic signal inputs 74 communicatively connected to the regulator of the present invention. Further, control unit 70 may also be powered via a battery or plug-in power source, and thereby include a separate power line connected to the regulator of the present invention, for certain embodiments where the regulator does not include its own power source.

Accordingly, the present invention also includes a method of controlling flow of a therapeutic gas to a gas delivery system. The method may include the steps of attaching a gas regulator to a gas source, wherein the regulator has a gas inlet and outlet, and the gas source includes a NFC tag having data indicative of at least one information item recorded in the memory of the NFC tag, and opening the gas source to allow the gas to flow into the inlet of the regulator. The method also may include reading the at least one information item resident in the NFC tag and transmitting the data to a gas delivery system control unit communicatively connected to the regulator. The method may also include sensing the pressure of gas entering the regulator from the gas source and transmitting data indicative of the sensed pressure to the gas delivery system control unit communicatively connected to the regulator. Lastly, the method includes delivering gas exiting the regulator to the gas delivery system based on the at least one information item.

The present invention also includes a method of entering at least one information item relating to a gas source to a gas delivery system control unit. The method may include providing a gas source having a NFC tag that includes at least one information item stored in a memory of the NFC tag, attaching a regulator that includes a NFC sensor, wherein the NFC sensor is positioned to read the NFC tag when attached to the gas source, and transmitting the at least one information item read by the NFC sensor to a gas delivery system control unit.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A gas regulator, comprising:
   a housing;
   a gas inlet to the housing, the gas inlet having an attachment mechanism configured to attach to a valve assembly of a pressurized gas container holding a gas at a raised pressure;
   a gas outlet from the housing, the gas outlet in fluid communication with the gas inlet and configured for fluid communication with a gas delivery system;
   a pressure regulator within the housing; and
   a Near Field Communication (NFC) sensor within the housing configured for communication with the gas delivery system and configured to sense an NFC tag on the pressurized gas container when the NFC sensor is positioned within 10 cm of the NFC tag.

2. The regulator of claim 1, further comprising a pressure sensor within the housing.

3. The regulator of claim 1, wherein the NFC sensor comprises a NFC reader.

4. The regulator of claim 1, wherein the regulator is configured for communicative connectivity to a gas delivery system control unit.

5. The regulator of claim 4, wherein the regulator is configured to transmit data read from the NFC tag to the gas delivery system control unit.

6. The regulator of claim 5, wherein the data read from the NFC tag is selected from the group consisting of gas type, gas concentration, gas volume, gas expiration date, gas container owner, gas container size, and gas tank inspection dates.

7. The regulator of claim 4, wherein the regulator is configured to transmit a signal indicative of sensed pressure by the pressure sensor to the gas delivery control unit.

8. The regulator of claim 6, wherein the pressure regulator is controlled by the control unit.

9. The regulator of claim 7, wherein the pressure regulator is controlled by the control unit.

10. The regulator of claim 1, further comprising a pressure gauge.

11. The regulator of claim 1, wherein the pressurized gas container comprises a therapeutic gas.

12. A method of entering at least one information item relating to a pressurized gas source to a gas delivery system control unit, comprising the steps of:
    providing a pressurized gas source holding a gas at a raised pressure, the pressurized gas source having a NFC tag that includes at least one information item stored in a memory of the NFC tag;
    attaching the regulator of claim 1 to the pressurized gas source, wherein the NFC sensor of the regulator is positioned to read the NFC tag when attached to the pressurized gas source;
    reading the at least one information item via the NFC sensor; and
    transmitting the at least one information item read by the NFC sensor to a gas delivery system control unit.

13. The method of claim 12, wherein the at least one information item is selected from the group consisting of gas type, gas concentration, gas volume, gas expiration date, gas container owner, gas container size, and gas tank inspection dates.

14. The method of claim 12, further comprising sensing the pressure of gas from the pressurized gas source via a pressure sensor positioned in the regulator, and transmitting a signal indicative of the sensed pressure to the gas delivery system control unit.

15. The method of claim 12, wherein the pressurized gas source comprises a therapeutic gas.

16. A method of controlling flow of a pressurized therapeutic gas to a gas delivery system, comprising the steps of:
    providing a pressurized gas source having a gas at a raised pressure, the pressurized gas source having a NFC tag that includes at least one information item stored in a memory of the NFC tag;
    attaching a regulator that includes a NFC sensor within a housing, wherein the housing of the regulator includes a gas inlet and outlet and is in fluid communication with a gas delivery system, and wherein the NFC sensor within the regular housing is positioned to read the NFC tag when the regulator is attached to the pressurized gas source and within 10 cm of the NFC tag;
    reading the at least one information item via the NFC sensor;
    transmitting the at least one information item read by the NFC sensor to a gas delivery system control unit; and
    controlling the flow of pressurized gas based on the transmitted at least one information item.

17. The method of claim 16, wherein the at least one information item is selected from the group consisting of gas type, gas concentration, gas volume, gas expiration date, gas container owner, gas container size, and gas tank inspection dates.

18. The method of claim 16, further comprising sensing the pressure of gas from the pressurized gas source via a pressure sensor positioned in the regulator, and transmitting a signal indicative of the sensed pressure to the gas delivery system control unit.

* * * * *